US006585991B1

(12) United States Patent
Rojas et al.

(10) Patent No.: US 6,585,991 B1
(45) Date of Patent: Jul. 1, 2003

(54) TERMITE BAIT MATRIX

(75) Inventors: Guadalupe M. Rojas, Metairie, LA (US); Juan A. Morales-Ramos, Metairie, LA (US); Edgar G. King, Jr., Greenville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 45 days.

(21) Appl. No.: 09/625,940

(22) Filed: Jul. 26, 2000

Related U.S. Application Data

(63) Continuation of application No. 09/294,499, filed on Apr. 20, 1999, now abandoned.

(51) Int. Cl.$^7$ ............................................. A01N 25/10
(52) U.S. Cl. ..................... 424/410; 424/84; 424/405; 424/409; 424/413; 424/484; 424/DIG. 11; 514/57; 514/78; 514/167; 514/558; 514/561; 514/669; 514/724; 514/725
(58) Field of Search .................... 424/DIG. 11, 84, 424/405, 407, 409, 410, 413, 484–488; 514/57, 724, 325, 558, 78, 167, 561, 669

(56) References Cited

U.S. PATENT DOCUMENTS

| | | | | |
|---|---|---|---|---|
| 4,363,798 A | * | 12/1982 | D'Orazio ..................... | 424/84 |
| 4,755,397 A | * | 7/1988 | Eden et al. ............... | 427/213.3 |
| 4,983,390 A | * | 1/1991 | Levy ......................... | 424/404 |
| 5,232,940 A | * | 8/1993 | Hatton et al. ................ | 514/407 |
| 5,464,613 A | * | 11/1995 | Barcay et al. ................ | 424/84 |
| 5,637,298 A | * | 6/1997 | Stowell ....................... | 424/84 |
| 5,747,519 A | * | 5/1998 | Kodama et al. ............ | 514/407 |
| 5,874,097 A | * | 2/1999 | Henderson et al. ......... | 424/405 |
| 5,962,119 A | * | 10/1999 | Chan ...................... | 428/537.7 |

FOREIGN PATENT DOCUMENTS

| | | | |
|---|---|---|---|
| EP | 0431468 | * | 6/1991 |
| GB | 2130264 | * | 5/1984 |
| WO | 9000005 | * | 1/1990 |
| WO | 93/23998 | * | 12/1993 |

OTHER PUBLICATIONS

Napier, Kristine, "Fat Replacers The Cutting Edge of Cutting Calories", Prepared for the American Council on Science and Health, Oct. 1997, pp. 1–29.
Fat Replacers—ADA Position, J. Am. Diet. Assoc.,Position Statement, 1998, 98:463–468,Retrieved from the Internet: on May 14, 2002 <URL: http://www.eatright.org/adapt/498.html.
International Fiber Corporation, Retrieved from the Internet on May 14, 2002: Company History <URL: http://www.ifcfiber.com/company.history.html; Breads <URL: http://www.ifcfiber.com/applications/food/breads.html; Solka–F-LOC <URL: http://www.ifcfiber.com/products/solkafloc.html; Justfiber <URL: http://www.ifcfiber.com/products/justfiber.html; Vegetable Derived from Baboo & Vegetable Fiber Derived From Cotton Seed, URL: http://www.ifcfiber.com/products/vegetable.html.
5894–Purified Diet for Primates, Retrieved from the Internet on May 14, 2002 URL<http://www.testdiet.com/5894.htm.
DMH Ingredients–Powdered Cellulose, Retrieved from the internet on May 14, 2002 URL< http://www.dmhingredients.com/cat_06.htm.
Moore, Cindy Tittle, Miscellaneous Information including "Low fat, high fiber", originally written 1991 & updated through 1997, maintained by the Fanciers website as of Jul. 1999, retrieved from the Internet May 14, 2002: <URL: http://www.fanciers.com/cat–faqs/misc.shtml.
Bon Appétit p. 32, 34, 66, Dec. 1998.*

* cited by examiner

*Primary Examiner*—Neil S. Levy
(74) *Attorney, Agent, or Firm*—John D. Fado; Randall E. Deck

(57) ABSTRACT

Termite foods mixed together in a matrix suitable to be used as baits and attractants for termites are provided. This termite matrix is preferred by termites over naturally-occurring foods such as deadwood, trees and wood used in human constructions, and other known termite matrices. It comprises cellulose, water and termite-preferred nutrients. Methods of monitoring the presence of termites using such matrices, and methods of controlling termites using such matrices to deliver termite toxins are also provided.

21 Claims, No Drawings

TERMITE BAIT MATRIX

CROSS REFERENCE TO RELATED APPLICATIONS

This application is a continuation of application Ser. No. 09/294,499, filed Apr. 20, 1999, for which the status is now ABD.

BACKGROUND OF THE INVENTION

This invention relates to a nutritionally based baiting composition and methods for its use in the monitoring and control of termites.

Damage in the United States attributable to subterranean termites is now estimated to be in excess of one billion dollars a year. All wooden or wood-containing structures are potentially affected, including homes, outbuildings, fences, utility poles, railway sleepers, boats, bridges, retaining walls and even living trees. Since their introduction to the United States within the last half-century, Formosan subterranean termites, *Coptotermes formosanus*, have become one of the most destructive pests in the contiguous United States. Reasons for this include their massive colonies which can contain tens of millions of individuals, their ability to attack several species of living trees, and their high level of reproduction.

The most successful existing methods for control of subterranean termites are preventive rather than remedial. These include barrier treatments to structures and the pre-emptive treatment of wood materials with chemicals to prevent termite attack. These however have drawbacks. Physical barriers are not compatible for retrofitting on many existing constructions and may not be completely effective, and chemical treatments are only partially effective and last only about five years.

Low toxicity baits utilizing growth regulators have shown success in reducing damage caused by subterranean termites, with hexaflumuron having been particularly effective in suppressing large colonies of *C. formosanus*. Utilized matrices for the baits have consisted of cardboard, filter paper, pine wood or pure cellulose. These matrices have, however, all suffered from generating less than optimal responses from the termites, which have in varying degree bypassed them in favor of other sources of cellulose such as houses and trees.

While various methodologies and compositions exist for the monitoring and control of termites, there remains a need for the creation of improved tools in this area.

Therefore, it is an object of this invention to provide a bait matrix composition effective as a toxicant delivery system for termites.

Another object is to provide a composition which may be used for the monitoring of termites.

Yet another object is to provide compositions and methods for the effective control of termite populations.

SUMMARY OF THE INVENTION

We have discovered that termites may be more effectively monitored and/or controlled through use of a nutritionally-based matrix which works as an attractant and carrier for chemicals which are toxic to termites. A termite matrix containing nutritionally requisite components enhances its usefulness as a bait and an attractant for termites. The termite matrix of this invention is preferred by termites over naturally-occurring foods such as deadwood and trees, wood and cellulose-based products used in human constructions, and other known termite foods such as cardboard. The matrix comprises cellulose as a primary component, since cellulose serves as the basis of the termite's normal diet. In addition it contains termite-preferred nutrients, i.e., nutrients required for termite growth and development. These nutrients are selected and present in the termite matrix of this invention in such amounts that the termite matrix is preferred by termites over alternate available food sources such as wood and other termite foods known to the art. The invention is premised on applicants' discovery that termites have the ability to finely discriminate between food sources on the basis of their nutritional value.

In addition to cellulose and water, the termite bait matrix of this invention preferably comprises lipids, vitamins and amino acids required by termites, termite growth factors, as well as feed-conditioning agents which simulate smells and tastes of fermenting food.

Termites for which the termite matrix of this invention is useful include all termite species belonging to the families Rhynotermitidae and Kalotermitidae, preferably *Coptotermes formosanus* and *Reticulitermes flavipes*.

The termite matrix of this invention, also referred to herein as the "bait matrix" or "termite food," may be used to attract termites to the site in which it is placed for purposes of counting and monitoring the size and presence of termite populations.

The matrix may also be used as a highly effective carrier for enhancing the delivery of termite toxins for the purpose of destroying substantial numbers of termites and thus inhibiting termite damage to cellulosic structures such as buildings and trees.

Methods of making termite-preferred matrices of this invention are also provided comprising mixing the various components to form a food, and preferably including the steps of separately mixing autoclavable components (including ethyl alcohol), autoclaving, and adding components which do not tolerate heat such as yeast hydrolysate. The method need not include heat sterilization but preferably does, since water may contain fungal spores which can make the matrix less attractive to termites if they do not discover it immediately after it has been placed in a bait station and the spores have a chance to grow. The method may also include adding termite toxins to the matrix and encasing this matrix in a physical container or a coating material. The container or coating material should be made of a water-retentive, vapor-permeable material.

Methods of killing termites are also provided comprising placing a toxin-containing matrix in a termite habitat upon which the termites will preferentially feed in place of other environmentally-available food sources. The methods preferably also include placing hydrated water-retaining materials (also referred to herein as water-retention agents) within the termite bait matrix or in the area immediately surrounding the termite matrix to provide a degree of humidity to the immediate area which can be detected by termites serve as a second means of attracting them.

Methods of monitoring termite activity in a region are also provided comprising placing a termite bait matrix as described above (referred to herein as a "bait station") at one or more locations in a region and assessing the presence of termites at the site.

Methods of attracting termites comprising a hydrated water-retention agent in a termite habitat are also provided.

A termite attractant comprising a hydrated water-retention agent contained within a termite-accessible container is also provided. The "termite-accessible container" refers to a container or coating which retains moisture inside but which termites can enter.

DETAILED DESCRIPTION

A bait matrix composition for termites has been developed which sufficiently fulfills the nutritional needs of the Formosan and native subterranean termites so as to be preferred by termites to other environmentally available sources of cellulose such as cardboard and southern yellow pine. The matrix can be used in baiting systems to deliver termite toxins to termites. The matrix composition comprises cellulose, water, and termite-preferred nutrients.

The cellulose may be supplied by means of any cellulose-containing material, preferably having 90% to greater than 95% cellulose, so long as it does not include chemicals which are toxic or repellant to termites. Such materials include commercially available cellulose, wood, paper, and cardboard, and are preferably in particulate form for ease of mixing with the other ingredients of the matrix. Sawdust may be from any plant source but is preferably from woods preferred by termites such as maple, birch, sweet gum and related woods. Alternate sources of sawdust, while usable, may contain chemicals in amounts that reduce the utility of such sawdust materials due to either repellant or toxic effects. Preferably, commercially available cellulose powder is used because it is less expensive than sawdust and lacks such chemicals.

Termites prefer foods which are at least partially broken down, as by fermentation, and have pH levels produced by fermentation, i.e., less than about 5, and preferably less than about 4.5. These conditions favor the microorganisms contained in termite guts, including protozoans and bacteria, which break down and digest cellulose. The termite body surface also carries fungal spores which in nature infect the food material and, after a period of time in which fungal growth is established, render it more nutritious. Thus fresh wood material is not a preferred termite food. The termite matrices of this invention possess both appropriate pH and odors indicative of ongoing fermentation processes, both of which serve to attract termites.

The termite matrices of this invention therefore preferably comprise feed-conditioning substances (or breakdown products thereof) which cause the matrices to simulate natural termite foods having a degree of fermentation (infestation with microorganisms and their products), which is attractive to termites. Through use of such conditioning agents, the matrices emit smells attractive to termites. Such conditioning agents include pH-adjusting agents such as hydrochloric, acetic or other acids which are not toxic to termites in the amounts used, present in quantities sufficient to lower the pH of the food to 5 or less. Ethyl alcohol is also used for its ability to dissolve fats and sterols and attract termites. The ethyl alcohol is used in amounts sufficient for its effects to be detected by termites but at a level that does not interfere with the growth of essential microorganisms in the matrix, with this being in an amount ranging from about 0 to about 8 ml/kg of matrix. Preferably, ethyl alcohol is used in amounts between about 0.5 and about 8 ml/kg of matrix. As will be understood by those skilled in the art, if the matrix is heat-sterilized prior to use, the volatile alcohol will evaporate; however, the matrix will contain products resulting from action of the alcohol on other components. Yeast hydrolysate is also a preferred conditioning substance.

If no feed-conditioning substances are used, a period of two or three weeks, depending on the ambient temperature, should be allowed for fermentation to occur to make the matrix attractive to termites.

The degree to which the presence of a particular component causes termites to prefer a food over other foods not containing the component, or containing greater or lesser amounts thereof, may readily be assessed using methods described herein.

The matrix also may comprise vitamins and amino acids characteristic of naturally-occurring termite food or attractive to termites, including vitamins such as riboflavin, D-biotin, choline chloride, vitamin B-12, folic acid, myo-inositol, nicotinamide, calcium pantothenate, pyridoxal hydrochloride, thiamine and ascorbic acid; and amino acids such as L-glutamic acid, L-histidine, L-glutamine, L-alanine, L-lysine, L-isoleucine, L-proline, and L-tyrosine. Vitamin and amino acid-containing materials include yeast and yeast hydrolysate, as well as synthetic solutions that contain these chemicals. Yeast hydrolysate is preferred because of its ability to also act as a food conditioning agent. The vitamins and amino acids may be present in the food at aggregate ratios sufficient to be detectable by termites up to amounts which cause these insects to stop feeding. In the case of yeast hydrolysate, preferred amounts are between about 0.1 g/kg and about 3 g/kg of matrix, more preferably from about 1.0 g/kg of matrix to about 2.0 g/kg of matrix, and most preferably about 1.5 g/kg of matrix. Although it is not necessary that any particular vitamin or amino acid be present in detectable amounts, the aggregate amount of vitamins and amino acids should be present in amounts sufficient to cause the termites to exhibit a preference for foods containing these substances over their ordinary wood diet.

The termite matrix of this invention preferably contains a lipid, preferably a fat or phospholipid which is a source of choline chloride and fatty acids such as linolenic, palmitic, palmetoleic and oleic acids, which are most preferably found in lecithin. Vegetable oils such as corn oil, soybean oil, cotton oil, and other oils known to the art may also be used, as these contain desirably fatty acids such as linolenic acid. If oils such as these not containing choline chloride are used, choline chloride may be added separately to the matrix. The concentration of lipid in the matrix is sufficient to be detectable by termites and less than that causing termite refusal of the food. In the case of lecithin, this amount ranges from about 0.1 g/kg of food to about 12.5 g/kg of matrix, preferably from about 1 g/kg of matrix to about 2 g/kg of matrix, and is most preferably about 1.25 g/kg of matrix.

The matrix may comprise a growth factor required for termite growth, reproduction, and/or chitin formation. Preferably, the growth factor is ergosterol, a sterol produced by fungal infection of food materials by spores carried on the termite body, which emits a characteristic smell attractive to termites. Other useful growth factors include fatty acids and amino acids, such as the nutrients described above, and preferably linolenic acid. The growth factor should be present in an amount sufficient to be detectable by termites, but not so great as to be toxic or cause termites to refuse to feed on the matrix. In the case of ergosterol, the ratio of ergosterol to food is preferably between about 0 and about 4.5 g/kg of matrix, more preferably from about 0.2 g/kg of matrix to about 1.0 g/kg of matrix, and most preferably is about 0.45 g/kg of matrix.

The matrix may further comprise salts useful to termites such as calcium chloride, cobalt chloride, ferric chloride, zinc chloride, potassium phosphate, sodium phosphate, magnesium sulfate, copper sulfate, and manganese sulfate.

Amounts of salts may vary. Salts are preferably present in the food in amounts sufficient to that the aggregate ratio of salts to matrix is sufficient to cause the termites to exhibit a preference for the matrix. A good source of such salts is commercially available bottled drinking or spring water, preferably below a pH of about 6, which can be used to provide the requisite moisture for the matrix. Barbe's® water, available from Barbe's Dairy Company, West Wego, La., is a preferred water to supply salts to the matrix.

Subterranean termites prefer moist foods. To be more attractive than other available foods in the environment, the matrix of this invention must be moist. Enough water should be used to allow mixing of the matrix material, and/or completely hydrate the particulate or solid cellulose materials and to provide excess water to maintain a humid environment. In general about three-fourths by weight of the matrix should be water, but this may vary with the water content ranging from about 50% to about 90% by weight of the composition.

To ensure an acceptable moisture level in the matrix material as well as to serve as another means for termite attraction, a water-retention agent capable of absorbing water and releasing it slowly to the environment is used. Examples of such materials include agar and polyacrylamide, but may include any substance not otherwise possessing a repellant effect. Examples of preferred usable materials include the polyacrylamides such as Terrawet® T-400, Terrawet Company, San Diego, Calif., used in greenhouses which can absorb and retain up to a thousand times their own weight in water. These materials should be hydrated, preferably fully-hydrated, with the addition of at least three times their weight in water. The hydrated water-retaining materials may be mixed in with the matrix.

The inventors have discovered that termites are attracted during their foraging to high humidity conditions, preferably at least about 80% humidity, and more preferably at least about 90% humidity. Thus, moisture-retaining material as described above is preferably placed in the immediate environment of the bait matrix to provide a humidity readily detectable by and attractive to termites. In a preferred embodiment in which a polyacrylamide such as Terrawet® 400 is used as the water-retaining agent, it may be placed in the area of a termite bait or monitoring station at an application rate effective for eliciting an attractive response, which for a polyacrylamide ranges from about 1 g to about 10 g (dry weight) per square foot. The hydrated polyacrylamide, preferably hydrated to a water:polymer weight ratio of at least about 30:1, can be injected into the soil around the bait station by pressure using commercially available injectors, preferably to a radius around the bait matrix of at least about 2.5 cm. Other water-retaining agents as described above can alternatively be used, adjusting ratios to achieve 80% to 90% humidity as will be readily apparent to those skilled in the art.

The termite matrix of this invention may be used to attract termites to its immediate environment for purposes of monitoring the size and presence of termite populations, e.g., by observing termites and counting or otherwise estimating the number of termites present by measuring the consumption of matrix. Typical monitoring strategies utilize approximately one bait station per 10–15 linear feet. The significantly faster response of termites to the bait matrix of this invention compared to the pine wood conventionally used results in enhanced monitoring efficacy, and means that shorter periods between inspections may be required than is the case with pine wood. Additionally, the bait matrix of this invention may be used in combination with a preferred wood or yellow pine wood to extend the period of termite activity at the monitoring site.

The termite matrix of this invention may also be used as a carrier for any conventional termite toxin such as hexaflumuron, imidacloprid and 5-amino-1-[2,6-dichloro-4-(trifluoromethyl)phenyl]- 4-[(3-fluoromethyl)-sulfonyl]-1-H-pyrazole-3-carbonitride (referred to herein as "fipronil") of Chem Service, Inc., West Chester, Pa. Other bioactive compounds not conventionally recognized as termite toxicants may also be used as termiticides. These include streptomycin sulfate, rifampicin, albendazole, neomycin sulfate, sorbic acid, and commercially available antimycotics such as antibiotic antimycotic available from Sigma Company, St. Louis, Mo. For biocidal efficacy, toxins must be present in amounts less than those detectable by termites, with this amount typically being less than about 1000 ppm for hexaflumuron, imidacloprid, and fipronil and other antimicrobials. Due to the high rate of consumption induced by the feed matrix of the instant invention, satisfactory kill of termites can be achieved with toxicant concentrations well below the rejection threshold. Useful amounts typically range from about 1 ppm to about 200 ppm of the bait composition. Preferred concentrations, while being readily determinable by conventional methods, are typically about 25 to about 50 ppm for hexaflumuron, about 1 to about 5 ppm for imidacloprid and fipronil, and about 5 to about 12.5 ppm for other antimicrobials.

The matrix materials of this invention, with or without toxins, may be encased in materials or containers which are water-retentive such that they substantially prevent evaporation of the moisture in the food, but which are vapor-permeable to a degree sufficient to allow termites to detect odors coming from the matrix. Suitable materials may be readily determined by the practicing artisan and include hard waxes with low melting points such as paraffin or beeswax in which pieces of the matrix material can be dipped or which can be otherwise coated on the matrix, and moldable polymers such as styrofoam, and polyurethane foams such as Great Stuff®, Flexible Products Company, Joliet, Ill. Fibrous casing tubes for sausages such as those available from L.E.M. Products, Inc., Miamitown, Ohio, which consists of cotton fibers coated with wax, turned inside out so as not to present the wax surface to the termites, are also preferred materials to be used for containers for the matrices of this invention.

EXAMPLES

Example 1

Nutritional Content of Naturally-occurring Termite Foods

Based on studies reported by King, E. G., Jr. and Spink, W. T. (1974), "Laboratory studies on the biology of the Formosan subterranean termite with primary emphasis on young colony development," *Ann. Entomol. Soc. Amer.* 67:953–958, and upon chemical analysis via High Performance Liquid and Gas Chromatography of components of healthy and infested yellow pine, water oak and weeping willow, relative amounts of mineral salts, vitamins, fatty acids, sterols and amino acids typically found in favored naturally-occurring termite diets were determined and 1L stock solutions prepared as described in Tables 1–4.

TABLE 1

Mineral Salt Solution

| Vendor | Chemical | Amount in g |
|---|---|---|
| | Cations | |
| Sigma C-2661 | Calcium chloride | 12 |
| Sigma C-8661 | Cobalt chloride | 2 |
| Sigma F-2877 | Ferric chloride.6H20 | 8 |
| Sigma Z-0152 | Zinc chloride | 2 |
| Lab. | Distilled water | 1000 ml |
| | Anions | |
| Sigma P-5655 | Potassium phosphate | 29.6 |
| Sigma S-5136 | Sodium phosphate | 4 |
| Lab. | Distilled water | 1000 ml |
| | Transition Metals | |
| Sigma M-2643 | Magnesium sulfate | 48 |
| Sigma C-8027 | Copper sulfate | 2 |
| Sigma M-1144 | Manganese sulfate | 0.4 |
| Lab. | Distilled water | 1000 ml |

TABLE 2

Vitamin Solution

| Vendor | Chemical | Amount g/L |
|---|---|---|
| Sigma R-9504 | Riboflavin | 0.2 |
| Sigma B-4639 | D-Biotin | 0.012 |
| Sigma C-7527 | Choline Chloride | 40 |
| Sigma V-6629 | Vitamin $B_{12}$ | 0.004 |
| Sigma F-8758 | Folic acid | 0.75 |
| Sigma I-7508 | Myo-Inositol | 3 |
| Sigma N-0636 | Nicotinamide | 1 |
| Sigma P-5155 | Ca pantothenate | 0.4 |
| Sigma P-6155 | Pyridoxal. HCl | 0.037 |
| Sigma T-1270 | Thiamine | 0.08 |
| Sigma A-4544 | Ascorbic acid | 2.4 |

TABLE 3

Amino Acid Solution

| Vendor | Chemical | Amount in mgs |
|---|---|---|
| Sigma G-5638 | L-Glutamic acid | 4.0 |
| Sigma H-9511 | L-Histidine | 12.0 |
| Sigma G-5763 | L-Glutamine | 20.0 |
| Sigma A-3534 | L-Alanine | 2.0 |
| Sigma L-1262 | L-Lysine | 4.0 |
| Sigma I-7383 | L-Isoleucine | 2.0 |
| Sigma P-4655 | L-Proline | 4.0 |
| Sigma T-1020 | L-Tyrosine | 28.0 |
| Lab. | Distilled water | 284.5 ml |

TABLE 4

Autoclavable portion for 300 ml medium

| Vendor | Chemical | Amount in g |
|---|---|---|
| Lab made | Amino acid solution | 284.5 ml |
| Difco 0140-01 | Bacto-Agar | 9 |
| Sigma E-6510 | Ergosterol | 0.18 |
| Quantum MT194A31 | Ethanol U.S.P. dehydrated | 1.5 |
| USB 18240 | Lecithin | 0.3 |

The salt solution of Table 1 was prepared by weighing out the listed chemicals in each group and placing them into a 1L glass beaker, adding 700 ml water and dissolving well, then bringing the mixture to volume using a 1L graduated cylinder. The solution was filter sterilized using a 0.22 micron nylon membrane filter (Corning #430773), transferred to sterile glass serum bottles and capped with sterile rubber sleeve stoppers. This mixture should be stored at about 1° C.

The vitamin solution of Table 2 was made by placing 700 ml of warm (28–30° C.) Milli-Q® distilled water from Barnstead Company, Fisher Scientific, Atlanta, Ga., into a 2L glass beaker, adding the riboflavin and mixing until completely dissolved. The solution was allowed to cool down to room temperature, 20–25° C., and the rest of the vitamins were added. Although the order of adding the vitamins is not critical, it is best if B-12 is added last because it so readily decomposes. The solution was diluted to 1L with distilled water using a glass graduated cylinder and filter sterilized as above, then transferred to sterile serum amber glass bottles and closed with a sleeve stopper. This mixture should be frozen for storage unless used immediately.

The amino acid solution of Table 3 was made by weighing out the amino acids listed and placing them into a 500 ml autoclavable glass bottle, then adding the distilled water and screwing the lid down loosely. The bottle was placed in a microwave set at high power for 3 min, then manually shaken to mix the amino acids. The bottle was placed in the microwave until the mixture began to boil (about one minute) and hand shaken again, then placed back in the microwave for thirty more seconds. The bottle of clear solution was closed with a lid and set aside.

To prepare 300 ml of the autoclavable portion of the medium, the ingredients of Table 4 were weighed out and added to the amino acid solution. After turning the bottle cap ¼ turn, the mixture was autoclaved at 120° C. for 20 min and allowed to cool down to 60° C. in a water bath set at 50° C.

Powdered cellulose from Bio-Serv Company, Frenchtown, N.J., No. 3425, was weighed out in a 600 ml glass beaker, tightly covered with foil and autoclaved as above.

The salt and vitamin solutions of Tables 1 and 2 were mixed with 0.3 g yeast hydrolysate from ICN Biochemicals Company, Cleveland, Ohio, and mixed with the autoclavable portion described above and the cellulose to form approximately 1 kg of matrix material about the consistency of bread dough. It is preferably molded into pieces of about 25 to about 500 g each using glass or Teflon molds. Glass molds may be used when no special shape is required. For example, glass petri dishes are suitable for forming wafer-shaped pieces. Because the material tends to stock to the molds, Teflone is preferred for more complex shapes. The molded materials are preferably wrapped in cheesecloth for ease of handling prior to encasing in the material used to form a container.

To form containers for the food material, paraffin was melted and maintained at 70° C. and pieces of the food material were dipped to cover them completely with a thin film about 1–2 mm thick. These were stored at room temperature.

Example 2

Component Preference Testing to Determine Reduced Bait Matrix

Materials expected to comprise the chemicals of Tables 1 and 2 were chosen and analyzed using High Performance Liquid Chromatography. Yeast hydrolysate was analyzed for its content of amino acids, vitamins and mineral salts, cations, anions, and transition metals. Lecithin was analyzed for its content of choline chloride and fatty acids. Barbe's® water available from Barbe's Dairy Company, West Wego, La., was analyzed for its content of mineral salts. Amounts of these materials providing types and amounts of components closely resembling those of Tables 1 and 2 were calculated and used to prepare the reduced matrix of this invention. The matrix of Example 1 was exposed to termite colonies and the consumption rate determined. Components of the reduced bait matrix were adjusted and adjusted versions of the reduced bait matrix were exposed to termite colonies until a consumption rate similar to that of the matrix of Example 1 was achieved.

Based on these tests, a reduced formula set forth in Table 5 was developed.

TABLE 5

Bait matrix composition

| Chemicals | Amount (g) |
|---|---|
| Lecithin | 1.250 |
| Ergoesterol | 0.450 |
| Ethyl alcohol | 3.750 |
| Water (Barbe's) adjusted to pH 4.5 with HCl | 735.000 |
| Cellulose | 250.000 |
| Polyacrylamide (T-400) | 0.187 |
| Yeast hydrolysate | 1.5 |
| Distilled water | 5.625 |

Example 3

Preparation of Reduced Bait Matrix

The bait matrix composition of Table 5 was prepared by weighing the lecithin, ergoesterol, ethyl alcohol and Barbe's water into a 1L glass bottle and mixing well using a glass bar. The opening of the bottle was covered with a foam stopper, the bottle cap was loosely placed on top of the stopper, and the stopper covered with foil. After autoclaving, the bottle was closed tightly and allowed to cool down. The cellulose was weighed into a second 1L glass beaker. The polyacrylamide was weighed into a third 1L glass beaker, distilled water was added and the beaker was tightly covered with foil. After autoclaving, the bottle was closed tightly and allowed to cool down. The beakers were tightly covered with foil and sterilized by autoclaving at 120° C. for 20 minutes.

Under a laminar flow hood, the yeast hydrolysate was added to the lecithin-containing mixture using a sterile spatula and the mixture was shaken until the yeast hydrolysate was incorporated. The bottle was tightly closed. If required, the mixture can be stored at this point at room temperature at least for a month.

Using a sterile spatula, the lecithin-containing mixture was added to the cellulose and mixed well. Finally, the polyacrylamide was added to the mixture and homogenized. The beaker was covered with foil and plastic to avoid contamination and loss of water. If required, this mixture can be stored at room temperature for at least a month. The mixture was compacted and divided into pieces of about 25–125 g each.

Example 4

Preference of Termites for Bait Matrix

Laboratory and field evaluations were performed to establish relative preference by the Formosan termite C. formosanus for the bait matrix of the instant invention as compared to southern yellow pine. In a laboratory evaluation, five termite colonies of variant population size had the base of a two-choice device attached for fluid communication thereto. These devices consisted of a 10 centimeter runway of transparent flexible PVC tubing attached to a plastic 'Y' connector whose two opposing ends were in turn attached by the same tubing to identical plastic containers (12.5×12.4×4 cm).

The paired containers were all filled with 80-ml of a 1:1 sand/topsoil mixture. One unit of each pair had a 25 gram bait matrix unit placed therein, while the other received two pieces of southern yellow pine wood with a similar combined weight. The bait matrix units were weighed again after the application of the paraffin to eliminate the paraffin weight. The wood samples were dried in a vacuum oven for 24 hours and exposed to a relative humidity of 95% for 1 hour before weighing.

Because the colonies were of different sizes, the devices were first exposed to the termite nests for eight days to establish consumption rates. Colonies 1 to 4 were then exposed to the devices for 27 days and colony 5 for 10 to 17 days based on observed consumption rates to compensate for variable colony sizes as larger colonies required more frequent change of matrix.

Subsequent to termite exposure, the matrix and wood samples were cleaned of soil and termites. The pine wood samples were again dried in the vacuum oven for 24 hours and exposed to a relative humidity of 95% for 1 hour. All samples were then reweighed. The daily consumption rates of bait matrix and pinewood were statistically compared by the general linear model (GLM) procedure using SAS statistical software.

This evaluation showed a highly significant difference in the consumption rates of the two substrates. The overall mean consumption rate of bait matrix was significantly higher than that of the pine wood ($F=45.73$; $df=1, 44$; $P<0.0001$). Because the five termite colonies used in this test were of different sizes, the consumption rates varied significantly. However, every one of the colonies showed a highly significant preference for the bait matrix over the pinewood (Table 6).

TABLE 6

Consumption rates (mg/day) of bait matrix and pine

| Nest | bait matrix | pine | N |
|---|---|---|---|
| 1 | 1231.2 ± 619.4 | 21.5 ± 14.7 | 4 |
| 2 | 550.1 ± 191.9 | 15.1 ± 14.0 | 4 |
| 3 | 912.4 ± 288.4 | 17.7 ± 18.6 | 4 |
| 4 | 417.0 ± 329.6 | 22.3 ± 16.4 | 4 |
| 5 | 1998.7 ± 687.4 | 85.2 ± 97.5 | 7 |

Example 5

Effects of Toxin on Preference of Termites for Bait Matrix (Laboratory)

To determine the acceptance by the Formosan subterranean termite of the bait matrix of Example 3 with toxic chemicals added, a pair choice test between a 25 g piece of yellow pine and an equivalent amount of bait matrix mixed with 50-ppm hexaflumuron was performed. Both pine and bait matrix were exposed to a Formosan termite colony composed of 1500 soldiers, workers, and nymphs, housed in a plastic Sterilite container containing 2L topsoil:sand (1:1)

at 40% relative humidity. The treatment box was maintained under dark conditions at 26±3° C. A control, 12" yellow pine wood stakes without hexaflumuron, was prepared and kept at the same conditions as the treatment.

The Formosan subterranean termite colony exposed to 50 ppm hexaflumuron reached 100% mortality in a period of 10 weeks which is equivalent to the report of Su and Scheffrahn (J. Econ Entomol. 89:1156–1160; 1996) at 125 ppm hexaflumuron in a matrix composed of spruce sawdust. No significant mortality was observed in the control. The above results indicates that the matrix of the instant invention is efficacious with regard to reducing toxicant treatment dosage.

Example 6

Effects of Toxin on Preference of Termites for Bait Matrix (Field)

A field test was implemented in the New Orleans City Park. One hundred sites 10 feet apart were chosen. In each site a piece of the matrix of Example 5 without toxicant encased in paraffin contained in a perforated plastic centrifuge tube was placed next to a 12" yellow pine wood stake as described in Example 5. After three weeks, 31 of the matrix sites were infested with subterranean termites, while only three of the stakes were infested. The sites that showed infestation on the wood stakes also presented infestation on the matrix preparations. Termites thus found ten times more of the sites using the bait matrix of this invention than using pine wood. This shows the C. formosanus termite prefers the matrix of this invention to yellow pine wood.

Example 7

Termite Toxins

Non-choice tests using five different antibiotics (streptomycin sulfate, rifampicin, albendazole, neomycin sulfate, and antimycotic) and a fungus inhibitor (sorbic acid) were conducted at four different concentrations (100, 250, 500, and 1000 ppm). Individual chemicals were mixed with the bait matrix of Example 3 at each concentration and 10 g samples of each were transferred to sterile plastic Petri dishes and exposed to groups of 20 termite workers and two soldiers. Five repetitions per treatment were done. The dishes were kept in a Percival incubator under dark conditions at 27±1° C. and 80% relative humidity. A control containing no antibiotic or fungus inhibitor was prepared and kept under the same conditions as the treatments. Time required to reach 100% mortality was recorded.

The non-choice tests showed that any of these six chemicals at 1000 ppm concentrations produced termite mortalities above 50% after three weeks of exposure. The mortality of the control was below 45%. The data showed that the lowest concentrations (100 ppm) of neomycin sulfate, albendazole, and sorbic acid produced mortality levels of 40, 40, and 33%, respectively after three weeks of exposure. The mortality of the control was 7%. Approximately 100% mortality was reached after five weeks of exposure in all the treatments, at which time the mortality of the control was 20%.

Example 8

Laboratory and field evaluations are being performed to establish relative preference by the Formosan termite C. formosanus for locales in which hydrated polyacrylamide has been placed as compared to sand. In a laboratory evaluation, five termite colonies of variant population size have the base of a two-choice device attached for fluid communication thereto. These devices consist of a 10 centimeter runway of transparent flexible PVC tubing attached to a plastic 'Y' connector whose two opposing ends are in turn attached by the same tubing to identical plastic containers (12.5×12.4×4 cm).

The paired containers are all filled with 80-ml of a 1:1 sand/topsoil mixture. One unit of each pair is filled with a mixture of sand: polyacrylamide: water (500:0.090:70) by weight, while the other contains only sand. Southern yellow pine wood with a similar combined weight is placed in both containers. The pieces of wood are weighed before exposure to the termites. Wood samples are dried in a vacuum oven for 24 hours and exposed to a relative humidity of 95% for 1 hour before weighing.

Because the colonies are of different sizes, the devices are first exposed to the termite nests for eight days to establish consumption rates. Colonies are then exposed to the devices for different periods of time based on observed consumption rates to compensate for variable colony sizes.

Subsequent to termite exposure, the wood samples are cleaned of soil and termites. The pine wood samples are again dried in the vacuum oven for 24 hours and exposed to a relative humidity of 95% for 1 hour. All samples are then reweighed. The daily consumption rates of bait matrix and pinewood are statistically compared by the general linear model (GLM) procedure using SAS statistical software.

These experiments show that while termites find both sites at approximately the same time, they prefer to consume the pine wood in the container with the polyacrylamide over those pieces placed on sand only.

It is understood that the foregoing detailed description is given merely by way of illustration and that modifications and variations may be made therein without departing from the spirit and scope of the invention. For example, choice of specific components and their relative proportions in the matrix may readily be determined by those skilled in the art without undue experimentation using the teachings hereof.

What is claimed is:

1. A solid phase termite bait matrix comprising:
   a) lecithin in an amount between about 0.1 and about 12.5 g/kg of said matrix;
   b) ergosterol in an amount ranging from about 0 to about 4.5 g/kg of said matrix;
   c) yeast hydrolysate in an amount between about 0.1 and about 3 g/kg of said matrix;
   d) ethyl alcohol in an amount ranging from about 0 to about 8 ml/kg of said matrix;
   e) cellulose in an amount of about 250 g/kg of said matrix; and
   f) the balance water.

2. The termite bait matrix of claim 1 further comprising:
   g) a water-retention agent in an amount between about 0 and about 0.05 g/kg of said matrix.

3. A method of monitoring termite activity in a region comprising:
   a) placing a termite bait matrix in said region, said termite bait matrix comprising:
      1) cellulose;
      2) water;
      3) a lipid preferred by termites, wherein said lipid is a source of choline chloride, fatty acids, or both; and
      4) one or more termite-preferred nutrients in amounts sufficient that said termite matrix is preferred by termites over wood; and b) assessing the presence of termites at the site of said termite matrix.

4. The method of claim 3 wherein said termite bait matrix further comprises a water-retention agent.

5. The method of claim 3 wherein said termite bait matrix is contained within a water-retentive, vapor-permeable coating or container.

6. The method of claim 3 wherein said termite bait matrix has a pH less than about 5.

7. The method of claim 3 wherein said termite bait matrix further comprises a feed conditioning substance or breakdown product thereof effective for simulating fermented termite foods and which is attractive to termites.

8. The method of claim 7 wherein said feed conditioning substance or breakdown product thereof is selected from the group consisting of pH adjusting agents, ethyl alcohol, yeast hydrolysate, and combinations thereof.

9. The method of claim 3 wherein said lipid is selected from the group consisting of lecithin and vegetable oils.

10. The method of claim 3 wherein said lipid is lecithin.

11. The method of claim 3 wherein said termite bait matrix comprises one or more termite growth factors selected from the group consisting of ergosterol and linolenic acid.

12. The method of claim 3 wherein said termite-preferred nutrients are selected from the group consisting of vitamins and amino acids.

13. The method of claim 3 wherein said termite-preferred nutrients are in the form of yeast or yeast hydrolsyate.

14. The method of claim 3 wherein said termite bait matrix further comprises a water-retentive, vapor-permeable barrier.

15. The method of claim 3 wherein said termite bait matrix is contained within a termite-accessible container or coating.

16. The method of claim 3 wherein said termite bait matrix further comprises a water retention agent.

17. The method of claim 3 wherein said water retention agent comprises agar or polyacrylamide.

18. The method of claim 3 wherein said water is present in said termite bait matrix in an amount between about 50 to 90% of said matrix, by weight.

19. The method of claim 3 wherein said cellulose is selected from the group consisting of sawdust and cellulose powder.

20. A method of monitoring termite activity in a region comprising:
   a) placing a solid phase termite bait matrix in said region, said termite bait matrix comprising:
      1) lecithin in an amount between about 0.1 and about 12.5 g/kg of said matrix;
      2) ergosterol in an amount ranging from about 0 to about 4.5 g/kg of said matrix;
      3) yeast hydrolysate in an amount between about 0.1 and about 3 g/kg of said matrix;
      4) ethyl alcohol in an amount ranging from about 0 to about 8 ml/kg of said matrix;
      5) cellulose in an amount of about 250 g/kg of said matrix; and
      6) the balance water; and
   b) assessing the presence of termites at the site of said termite matrix.

21. The method of claim 20 wherein said termite bait matrix further comprises a water-retention agent in an amount between about 0 and about 0.05 g/kg of said matrix.

* * * * *